(12) United States Patent
Ramachandran et al.

(10) Patent No.: US 10,018,571 B2
(45) Date of Patent: Jul. 10, 2018

(54) SYSTEM AND METHOD FOR DYNAMIC CARE AREA GENERATION ON AN INSPECTION TOOL

(71) Applicant: KLA-Tencor Corporation, Milpitas, CA (US)

(72) Inventors: Vijayakumar Ramachandran, Sunnyvale, CA (US); Ravikumar Sanapala, San Jose, CA (US); Vidyasagar Anantha, Hyderabad (IN); Philip Measor, San Jose, CA (US); Rajesh Manepalli, Telangana (IN); Jing Fang, Shanghai (CN)

(73) Assignee: KLA-Tencor Corporation, Milpitas, CA (US)

(*) Notice: Subject to any disclaimer, the term of this patent is extended or adjusted under 35 U.S.C. 154(b) by 65 days.

(21) Appl. No.: 15/166,591

(22) Filed: May 27, 2016

(65) Prior Publication Data

US 2016/0377561 A1 Dec. 29, 2016

Related U.S. Application Data

(60) Provisional application No. 62/198,911, filed on Jul. 30, 2015.

(30) Foreign Application Priority Data

May 28, 2015 (IN) ............................ 2681/CHE/2015

(51) Int. Cl.
*G01N 23/225* (2018.01)
*G01N 21/956* (2006.01)
(Continued)

(52) U.S. Cl.
CPC ... *G01N 21/9501* (2013.01); *G01N 21/95607* (2013.01); *H01L 22/20* (2013.01);
(Continued)

(58) Field of Classification Search
CPC .......... G01N 23/225; G01N 2223/646; G01N 2223/6116; G01N 2201/12; G01N 21/9501; G01N 21/956
See application file for complete search history.

(56) References Cited

U.S. PATENT DOCUMENTS 6,154,714 A 11/2000 Lepejian
6,529,621 B1 3/2003 Glasser et al.
(Continued)

FOREIGN PATENT DOCUMENTS

WO 20140149197 A1 9/2014

OTHER PUBLICATIONS

PCT International Search Report for PCT/US2015/034648 dated Sep. 13, 2016, 3 pages.

*Primary Examiner* — Sang Nguyen
(74) *Attorney, Agent, or Firm* — Suiter Swantz pc llo

(57) ABSTRACT

A defect inspection system includes an inspection sub-system and a controller communicatively coupled to the detector. The inspection sub-system includes an illumination source configured to generate a beam of illumination, a set of illumination optics to direct the beam of illumination to a sample, and a detector configured to collect illumination emanating from the sample. The controller includes a memory device and one or more processors configured to execute program instructions. The controller is configured to determine one or more target patterns corresponding to one or more features on the sample, define one or more care areas on the sample based on the one or more target patterns and design data of the sample stored within the memory device of the controller, and identify one or more defects within the one or more care areas of the sample based on the illumination collected by the detector.

47 Claims, 6 Drawing Sheets

(51) Int. Cl.
  *G01N 21/95* (2006.01)
  *H01L 21/66* (2006.01)
  *G01N 21/88* (2006.01)

(52) U.S. Cl.
  CPC ............... *G01N 2021/8854* (2013.01); *G01N 2021/95615* (2013.01); *G01N 2223/6116* (2013.01); *G01N 2223/646* (2013.01)

(56) References Cited

U.S. PATENT DOCUMENTS

| | | |
|---|---|---|
| 6,691,052 B1 | 2/2004 | Maurer |
| 6,748,103 B2 | 6/2004 | Glasser et al. |
| 6,920,596 B2 | 7/2005 | Sagatelian et al. |
| 6,921,672 B2 | 7/2005 | Satya et al. |
| 6,930,309 B1 | 8/2005 | Mankos et al. |
| 6,948,141 B1 | 9/2005 | Satya et al. |
| 6,966,047 B1 | 11/2005 | Glasser |
| 6,995,393 B2 | 2/2006 | Weiner et al. |
| 7,676,077 B2 | 3/2010 | Kulkarni et al. |
| 8,112,241 B2 | 2/2012 | Xiong |
| 8,126,255 B2 | 2/2012 | Bhaskar et al. |
| 8,194,968 B2 | 6/2012 | Park et al. |
| 8,611,639 B2 | 12/2013 | Kulkarni et al. |
| 8,781,781 B2 | 7/2014 | Kulkarni et al. |
| 2004/0115541 A1* | 6/2004 | Yamaguchi ............... G03F 1/84 430/30 |
| 2006/0159330 A1* | 7/2006 | Sakai ..................... G06T 7/001 382/141 |
| 2008/0167829 A1 | 7/2008 | Park et al. |
| 2009/0136121 A1* | 5/2009 | Nakagaki .............. G06T 7/0006 382/149 |
| 2009/0238441 A1* | 9/2009 | Yamashita ............. G06T 7/001 382/144 |
| 2011/0187848 A1 | 8/2011 | Choi et al. |
| 2012/0216169 A1 | 8/2012 | Park et al. |
| 2013/0182101 A1* | 7/2013 | Yong ........................ H04N 7/18 348/87 |
| 2013/0318485 A1* | 11/2013 | Park ..................... G06F 17/5081 716/102 |
| 2014/0105482 A1 | 4/2014 | Wu et al. |
| 2014/0199791 A1* | 7/2014 | Park ........................ H01L 22/12 438/14 |
| 2014/0199792 A1* | 7/2014 | Miyoshi ................. H01L 22/12 438/16 |
| 2015/0093014 A1* | 4/2015 | Goren ................. G01N 21/9501 382/149 |
| 2015/0125065 A1 | 5/2015 | Lee et al. |

\* cited by examiner

SYSTEM AND METHOD FOR DYNAMIC CARE AREA GENERATION ON AN INSPECTION TOOL

PRIORITY

The present application claims priority to India Provisional Patent Application No. 2681/CHE/2015, filed May 28, 2015, entitled NOVEL AND EFFICIENT APPROACH FOR ON-TOOL DYNAMIC CARE AREA GENERATION USING DESIGN, naming Vijayakumar Ramachandran, Vidyasagar Anantha, Philip Measor, and Rajesh Manepalli as inventors; and U.S. Provisional Patent Application No. 61/198,911, filed Jul. 30, 2015, entitled NOVEL AND EFFICIENT APPROACH FOR ON-TOOL DYNAMIC CARE AREA GENERATION USING DESIGN, naming Vijayakumar Ramachandran, Vidyasagar Anantha, Philip Measor, and Rajesh Manepalli as inventors, both of which are incorporated herein by reference in the entirety.

TECHNICAL FIELD

The present disclosure relates generally to defect inspection and, more particularly, to care area generation on an inspection tool.

BACKGROUND

Inspection systems identify and classify defects on semiconductor wafers to generate a defect population on a wafer. A given semiconductor wafer may include hundreds of chips, each chip containing thousands of components of interest, and each component of interest may have millions of instances on a given layer of a chip. As a result, inspection systems may generate vast numbers of data points (e.g. hundreds of billions of data points for some systems) on a given wafer. Further, the demand for ever-shrinking devices leads to increased demands on inspection systems. The demands include the need for increased resolution and capacity necessary to infer the root causes of identified defects without sacrificing inspection speed or accuracy.

However, the use of design data associated with the wafer typically impacts the overhead, and thus the throughput, of an inspection process. For example, a utility for the generation of care areas based on design data may provide large data files specifying various attributes of care areas that must be transferred to the inspection tool. Further, an inspection tool may need to register the design data with the sample to correlate the design coordinates with the coordinates of the inspection tool.

Therefore, it would be desirable to provide a system and method for curing shortcomings such as those identified above.

SUMMARY

A defect inspection system is disclosed in accordance with one or more illustrative embodiments of the present disclosure. In one illustrative embodiment, the system includes an inspection sub-system. In another illustrative embodiment, the inspection sub-system includes an illumination source configured to generate a beam of illumination. In another illustrative embodiment, the inspection sub-system includes a set of illumination optics to direct the beam of illumination to a sample. In another illustrative embodiment, the inspection sub-system includes a detector configured to collect illumination emanating from the sample. In another illustrative embodiment, the system includes a controller communicatively coupled to the detector. In another illustrative embodiment, the controller includes a memory device and one or more processors configured to execute program instructions. In another embodiment, the controller is configured to determine one or more target patterns corresponding to one or more features on the sample. In another embodiment, the controller is configured to define one or more care areas on the sample based on the one or more target patterns and design data of the sample. In another illustrative embodiment, the design data of the sample is stored within the memory device of the controller. In another embodiment, the controller is configured to identify one or more defects within the one or more care areas of the sample based on the illumination collected by the detector.

A defect inspection system is disclosed in accordance with one or more illustrative embodiments of the present disclosure. In one illustrative embodiment, the system includes an inspection sub-system. In another illustrative embodiment, the inspection sub-system includes an illumination source configured to generate a beam of illumination. In another illustrative embodiment, the inspection sub-system includes a set of illumination optics to direct the beam of illumination to a sample. In another illustrative embodiment, the inspection sub-system includes a detector configured to collect illumination emanating from the sample. In another illustrative embodiment, the system includes a controller communicatively coupled to the detector. In another illustrative embodiment, the controller includes a memory device and one or more processors configured to execute program instructions. In another embodiment, the controller is configured to determine one or more target patterns corresponding to one or more features on the sample. In another embodiment, the controller is configured to determine a source pattern. In another illustrative embodiment, the source pattern is proximate to a subset of instances of the one or more target patterns within design data of the sample. In another illustrative embodiment, the design data of the sample is stored within the memory device of the controller. In another illustrative embodiment, the controller is configured to define a spatial relationship between the source pattern and the at least one target pattern of the subset of instances of the one or more target patterns within the design data of the sample. In another illustrative embodiment, the controller is configured to identify one or more instances of the source pattern within the design data of the sample. In another illustrative embodiment, the controller is configured to identify the subset of instances of the one or more target patterns within the design data of the sample based on the one or more identified instances of the source pattern and the spatial relationship between the source pattern and the at least one target pattern of the subset of instances of the one or more target patterns. In another illustrative embodiment, the controller is configured to define one or more care areas on the sample based on the subset of instances of the one or more target patterns. In another illustrative embodiment, the controller is configured to identify one or more defects within the one or more care areas of the sample based on the illumination collected by the detector.

A defect inspection method is disclosed in accordance with one or more illustrative embodiments of the present disclosure. In one illustrative embodiment, the method includes providing design data of a sample to an inspection system. In another illustrative embodiment, the method includes determining one or more target patterns. In another illustrative embodiment, the one or more target patterns include design data associated with one or more sample features to be inspected. In another illustrative embodiment, the method includes defining one or more care areas on the sample by the inspection system based on the one or more target patterns and the design data of the sample. In another illustrative embodiment, the method includes identifying one or more defects within the one or more care areas of the sample.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF DRAWINGS

The numerous advantages of the disclosure may be better understood by those skilled in the art by reference to the accompanying figures in which.

DETAILED DESCRIPTION

Figure 1:
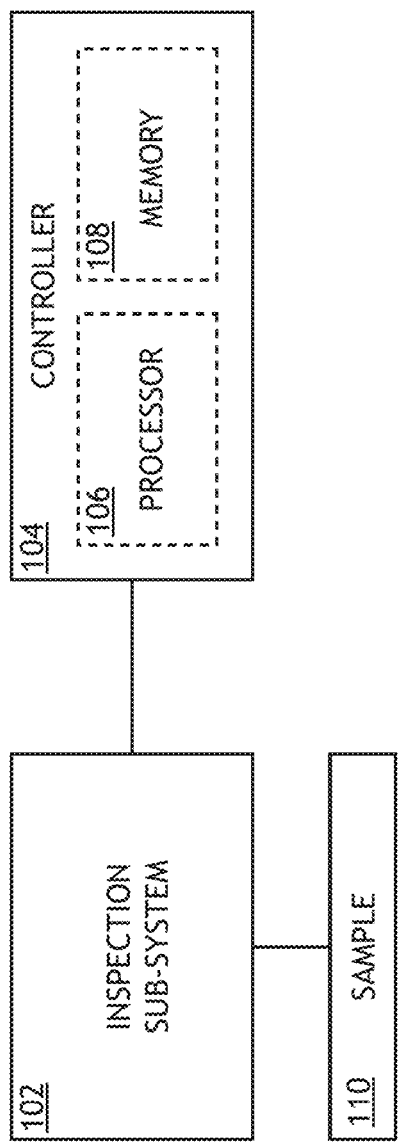
FIG. 1 is a conceptual view illustrating an inspection system, in accordance with one or more embodiments of the present disclosure.

Reference will now be made in detail to the subject matter disclosed, which is illustrated in the accompanying drawings.

Embodiments of the present disclosure are a directed to an inspection system with on-tool generation of care areas of a sample. In this regard, care areas, or select areas of the sample of interest for inspection, may be generated directly on the inspection tool. Additional embodiments of the present disclosure are directed to the on-tool identification of care areas based on identifying one or more instances of a target pattern of interest within design data of the sample stored on the inspection tool. For example, a target pattern may include design data associated with one or more sample features to be inspected. Additional embodiments of the present disclosure are directed to the storage and pre-processing of design data of a sample on an inspection system for efficient determination of care areas on the inspection tool. Further embodiments of the present disclosure are directed to the identification of a sub-set of instances of the target pattern within design data of the sample based on proximity to a source pattern within the design data. Accordingly, the generation of care areas may include a search of design data of the sample for a combination of a target pattern of interest filtered to include instances of the target pattern proximate to the source pattern based on a defined spatial relationship.

It is recognized herein that inspection tools may typically inspect only a subset of a surface of a sample for defects. The generation of care areas, or target regions of the sample to be inspected may significantly improve not only the efficiency of defect detection by reducing the inspected surface area, but also the accuracy of the defect inspection by reducing spurious signals and noise. Further, care areas may be defined to provide targeted inspection analysis such as, but not limited to, analysis of a particular defect type or the analysis of a particular pattern element located throughout the sample.

It is further recognized that design data of the sample (e.g. the physical layout of components on a sample, the electrical connections between components on the sample, or the like) may be utilized to define care areas. However, the use of design data typically impacts the overhead, and thus the throughput, of an inspection process. For example, a utility for the generation of care areas based on design data may provide large data files specifying various attributes of care areas (e.g. the location of each care area on a sample, the shape of each care area, and the like) that must be transferred to the inspection tool. Further, an inspection tool may need to register (e.g. align, scale, or the like) the design data with the sample to correlate the design coordinates (e.g. graphical design system (GDS) coordinates, or the like) with the coordinates of the inspection tool.

Embodiments of the present disclosure are directed to the storage of a pre-processed version of the design data of the sample on an inspection tool. In this regard, design-based care areas may be generated on the inspection tool using the pre-processed design data (e.g. a local version of pre-processed design data). Further, in some embodiments, design-based care areas may be generated on the inspection tool without further data transfer requirements. Additionally, design-based care areas generated on the inspection tool may be automatically aligned to coordinates of the inspection tool.

As used throughout the present disclosure, the term "sample" generally refers to a substrate formed of a semiconductor or non-semiconductor material (e.g. a wafer, or the like). For example, a semiconductor or non-semiconductor material may include, but is not limited to, monocrystalline silicon, gallium arsenide, and indium phosphide. A sample may include one or more layers. For example, such layers may include, but are not limited to, a resist, a dielectric material, a conductive material, and a semiconductive material. Many different types of such layers are known in the art, and the term sample as used herein is intended to encompass a sample on which all types of such layers may be formed. One or more layers formed on a sample may be patterned or unpatterned. For example, a sample may include a plurality of dies, each having repeatable patterned features. Formation and processing of such layers of material may ultimately result in completed devices. Many different types of devices may be formed on a sample, and the term sample as used herein is intended to encompass a sample on which any type of device known in the art is being fabricated. Further, for the purposes of the present disclosure, the term sample and wafer should be interpreted as interchangeable. In addition, for the purposes of the present disclosure, the terms patterning device, mask and reticle should be interpreted as interchangeable.

FIG. 1 is a conceptual view illustrating an inspection system 100, in accordance with one or more embodiments of the present disclosure. In one embodiment, the inspection system 100 includes an inspection sub-system 102 to detect defects on a sample 110.

It is noted herein that inspection sub-system 102 may be any type of inspection system known in the art suitable for detecting defects on a sample 110. For example, the inspection sub-system 102 may include a particle-beam inspection sub-system. Accordingly, inspection sub-system 102 may direct one or more particle beams (e.g. electron beams, ion beams, or the like) to the sample 110 such that one or more defects are detectable based on detected radiation emanating from the sample 110 (e.g. secondary electrons, backscattered electrons, luminescence, or the like). As another example, inspection sub-system 102 may include an optical inspection sub-system. Accordingly, inspection sub-system 102 may direct optical radiation to the sample 110 such that one or more defects are detectable based on detected radiation emanating from the sample 110 (e.g. reflected radiation, scattered radiation, diffracted radiation, luminescent radiation, or the like).

The inspection sub-system 102 may operate in an imaging mode or a non-imaging mode. For example, in an imaging mode, individual objects (e.g. defects) may be resolvable within the illuminated spot on the sample (e.g. as part of a bright-field image, a dark-field image, a phase-contrast image, or the like). In a non-imaging mode of operation, radiation collected by one or more detectors may be associated with a single illuminated spot on the sample and may represent a single pixel of an image of the sample 110. In this regard, an image of the sample 110 may be generated by acquiring data from an array of sample locations. Further, the inspection sub-system 102 may operate as a scatterometry-based inspection system in which radiation from the sample is analyzed at a pupil plane to characterize the angular distribution of radiation from the sample 110 (e.g. associated with scattering and/or diffraction of radiation by the sample 110).

In another embodiment, the inspection system 100 includes a controller 104 coupled to the inspection sub-system 102. For example, the controller 104 may be communicatively coupled to the detector 522. In this regard, the controller 104 may be configured to receive data including, but not limited to, inspection data from the inspection sub-system 102. In another embodiment, the controller 104 includes one or more processors 106. For example, the one or more processors 106 may be configured to execute a set of program instructions maintained in a memory device 108, or memory. The one or more processors 106 of a controller 104 may include any processing element known in the art. In this sense, the one or more processors 106 may include any microprocessor-type device configured to execute algorithms and/or instructions. Further, the memory medium 108 may include any storage medium known in the art suitable for storing program instructions executable by the associated one or more processors 106. For example, the memory medium 108 may include a non-transitory memory medium. As an additional example, the memory medium 108 may include, but is not limited to, a read-only memory, a random access memory, a magnetic or optical memory device (e.g., disk), a magnetic tape, a solid state drive and the like. It is further noted that memory medium 108 may be housed in a common controller housing with the one or more processors 106.

The inspection system 100 may utilize any inspection technique known in the art to detect defects associated with a sample. For example, defects on a sample 110 may be detected by comparing measured characteristics of the sample (e.g. generated by inspection sub-system 102, or the like) with measured characteristics of a reference sample (e.g. die-to-die (D2D) inspection, standard reference die (SRD) inspection, or the like). As another example, defects on a sample 110 may be detected by comparing an inspection image of the sample 110 with an image based on design characteristics (e.g. die-to-database (D2DB) inspection). As a further example, the inspection system 100 may include a virtual inspection system. In one embodiment, the controller 104 operates as a virtual inspector. In this regard, the controller 104 may detect one or more defects on the sample 110 by comparing persistent inspection data of the sample to persistent reference data (e.g. one or more reference images). For example, the inspection data and/or one or more reference images may be stored on the inspection system 100 (e.g. in memory 108) and utilized for defect detection. In another embodiment, the controller 104 generates and/or receives a simulated inspection image based on design data associated with the sample 110 to operate as a reference image for defect detection.

Inspection systems using design data are generally described in U.S. Patent Application no. 2014/0153814, published on Jun. 5, 2013, which is incorporated herein by reference in its entirety. Inspection systems using persistent data (e.g. stored data) are generally described in U.S. Pat. No. 8,126,255, issued on Feb. 28, 2012, which is incorporated herein by reference in its entirety. Inspection systems using design data of a sample to facilitate inspection is generally described in U.S. Pat. No. 7,676,077, issued on Mar. 9, 2010, and U.S. Pat. No. 6,154,714, issued on Nov. 28, 2000, which are incorporated herein by reference in their entirety. The determination of defect and fault sources are generally described in U.S. Pat. No. 6,920,596, issued on Jul. 19, 2005, U.S. Pat. No. 8,194,968, issued on Jun. 5, 2015, and U.S. Pat. No. 6,995,393, issued on Feb. 7, 2006, which are incorporated herein by reference in their entirety. Device property extraction and monitoring is generally described in U.S. Pat. No. 8,611,639, issued on Dec. 17, 2013. The use of dual-energy electron flooding for neutralization of a charged substrate is generally described in U.S. Pat. No. 6,930,309, issued on Aug. 16, 2005, which is incorporated herein by reference in its entirety. The use of reticles in inspection systems is generally described in U.S. Pat. No. 6,529,621, issued on Mar. 4, 2003, U.S. Pat. No. 6,748,103, issued on Jun. 8, 2004, and 6,966,047, issued on Nov. 15, 2005, which are incorporated herein by reference in their entirety. Generating an inspection process or inspection target is generally described in U.S. Pat. No. 6,691,052, issued on Feb. 10, 2004, U.S. Pat. No. 6,921,672, issued on Jul. 26, 2005, and U.S. Pat. No. 8,112,241, issued on Feb. 7, 2012, which are incorporated herein by reference in their entirety. Determination of critical areas of semiconductor design data is generally described in U.S. Pat. No. 6,948,141, issued on Sep. 20, 2005, which is incorporated by reference herein in its entirety.

Figure 2:
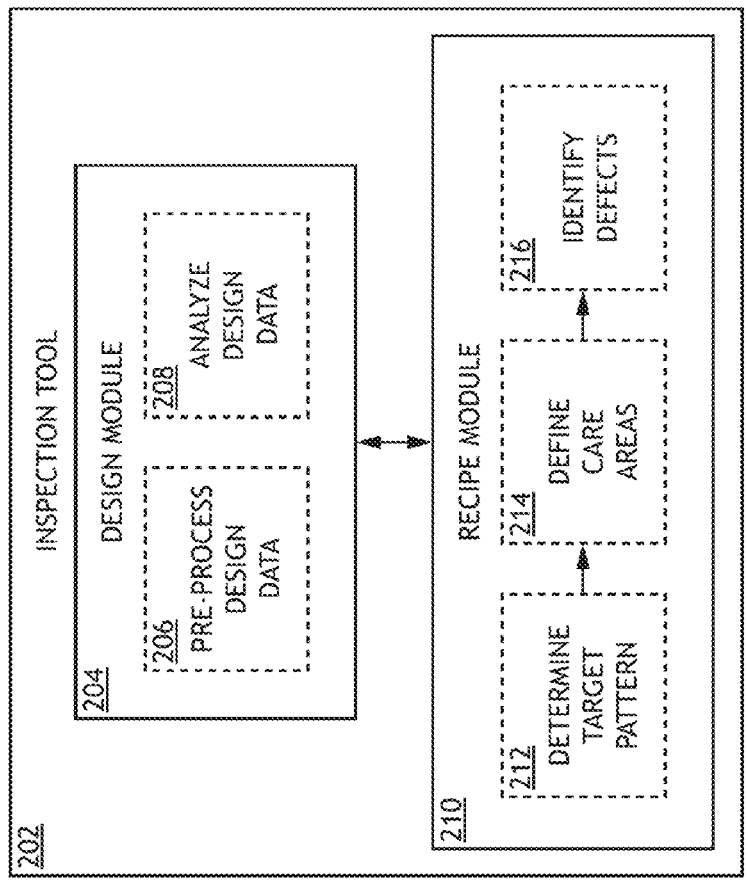
FIG. 2 is a block diagram of an inspection tool of an inspection system illustrating the use of design data to generate care areas for inspection based on design data stored on the inspection tool, in accordance with one or more embodiments of the present disclosure.

FIG. 2 is a block diagram of an inspection tool 202 of an inspection system 100 illustrating the definition of care areas on the inspection tool 202, in accordance with one or more embodiments of the present disclosure. In one embodiment, the inspection tool 202 includes one or more modules configured to perform one or more steps of the inspection tool 102. For example, the one or more modules of the inspection tool 202 may be, but are not required to be, implemented as one or more program instructions stored in memory 108 and executed by one or more processors 106.

In another embodiment, the inspection tool 202 includes a design module 204. For example, the design module 204 may include design data associated with one or more samples 110 to be inspected by the inspection tool 202. In this regard, care areas may be generated on the inspection tool 202 using design data associated with the sample 110. It is noted herein that the generation of design-based care areas directly on inspection tool 202 may facilitate efficient and dynamic generation of care areas. For example, the generation of design-based care areas on the inspection tool 202 may reduce data transfer (e.g. of care area definitions, or the like) between the inspection tool 202 and external systems. Further, the generation of design-based care areas on the inspection tool 202 may facilitate accurate alignment of coordinates associated with the design data to coordinates associated with the sample and/or the inspection tool 202. For example, design coordinates (e.g. GDS coordinates, or the like) may need to be adjusted (e.g. scaled, rotated, or the like) such that the size and orientation of design patterns of design data match printed patterns on the sample as measured by the inspection tool 202. The generation of design-based care areas on the inspection tool may facilitate accurate and efficient alignment the design and sample coordinate systems.

The term "design data" as used in the present disclosure generally refers to the physical design of an integrated circuit and data derived from the physical design through complex simulation or simple geometric and Boolean operations. In addition, an image of a reticle acquired by a reticle inspection system and/or derivatives thereof may be used as a proxy or proxies for the design data. Such a reticle image or a derivative thereof may serve as a substitute for the design layout in any embodiments described herein that uses design data. Design data and design data proxies are described in U.S. Pat. No. 7,676,007 by Kulkarni issued on Mar. 9, 2010; U.S. patent application Ser. No. 13/115,957 by Kulkarni filed on May 25, 2011; U.S. Pat. No. 8,041,103 by Kulkarni issued on Oct. 18, 2011; and U.S. Pat. No. 7,570,796 by Zafar et al. issued on Aug. 4, 2009, all of which are incorporated herein by reference. Further, the use of design data in directing inspection processes is described generally in U.S. patent application Ser. No. 13/339,805 to Park, filed on Feb. 17, 2012, which is incorporated herein by reference in the entirety.

Design data may include characteristics of individual components and/or layers on the sample 110 (e.g. an insulator, a conductor, a semiconductor, a well, a substrate, or the like), a connectivity relationship between layers on the sample 110, or a physical layout of components and connections (e.g. wires) on the sample 110. In this regard, design data may include a plurality of design pattern elements corresponding to printed pattern elements on the sample 110.

It is noted herein that design data may include what is known as a "floorplan," which contains placement information for pattern elements on the sample 110. It is further noted herein that this information may be extracted from the physical design of a chip usually stored in GDSII or OASIS file formats. The structural behavior or process-design interactions may be a function of the context (surroundings) of a pattern element. By using the floor plan, the analysis proposed can identify pattern elements within the design data, such as polygons describing features to be constructed on a semiconductor layer. Further, the proposed method may provide the coordination information of these repeating blocks as well as contextual data (e.g. the positions of adjacent structures, or the like).

In one embodiment, design data includes one or more graphical representations (e.g. visual representations, symbolic representations, diagrammatic representations, or the like) of pattern elements. For example, design data may include a graphical representation of the physical layout of components (e.g. descriptions of one or more polygons corresponding to printed pattern elements fabricated on the sample 110). Further, design data may include a graphical representation of one or more layers of a sample design (e.g. one or more layers of printed pattern elements fabricated on the sample 110) or the connectivity between the one or more layers. As another example, design data may include a graphical representation of electrical connectivity of components on the sample 110. In this regard, the design data may include a graphical representation of one or more circuits or sub-circuits associated with the sample. In another embodiment, design data includes one or more image files containing graphical representations of one or more portions of the sample 110.

In another embodiment, design data includes one or more textual descriptions (e.g. one or more lists, one or more tables, one or more databases, or the like) of the connectivity of pattern elements of the sample 110. For example, design data may include, but is not limited to, netlist data, circuit simulation data, or hardware description language data. Netlists may include any type of netlist known in the art for providing a description of the connectivity of an electrical circuit including, but not limited to physical netlists, logical netlists, instance-based netlists, or net-based netlists. Further, a netlist may include one or more sub-netlists (e.g. in a hierarchal configuration) to describe circuits and/or sub-circuits on a sample 110. For example, netlist data associated with a netlist may include, but is not limited to, a list of nodes (e.g. nets, wires between components of a circuit, or the like), a list of ports (e.g. terminals, pins, connectors, or the like), a description of electrical components between the nets, (e.g. resistor, capacitor, inductor, transistor, diode, power source, or the like), values associated with the electrical components (e.g. a resistance value in ohms of a resistor, a voltage value in volts of a power source, frequency characteristics of a voltage source, initial conditions of components, or the like). In another embodiment, design data may include one or more netlists associated with specific steps of a semiconductor process flow. For example, a sample 110 may be inspected (e.g. by system 100) at one or more intermediate points in a semiconductor process flow. Accordingly, design data utilized to generate care areas may be specific to the layout of the sample 110 at a current point in the semiconductor process flow. In this regard, a netlist associated with a particular intermediate point in a semiconductor process flow may be derived (e.g. extracted, or the like) from either the physical design layout in combination with a technology file (e.g. layer connectivity, electrical properties of each of the layers, and the like) or a netlist associated with a final layout of a sample 110 to include only components present on the wafer at the particular intermediate point in the semiconductor process flow.

In another embodiment, the design module 204 of the inspection tool 202 executes a step 206 of pre-processing design data. It is noted herein that design data may include data irrelevant to the determination of care areas of inspection system 100 (e.g. fabrication data, or the like). Further, design data may not be in a format suitable for efficient identification (e.g. searching, matching, or the like) of pattern elements of interest within the design data. Accordingly, pre-processed design data 206 may include a version of design data that is pre-processed to facilitate efficient generation of care areas on the inspection tool 202. In this regard, the pre-processed design data 206 may facilitate the identification of one or more instances of target patterns (e.g. pattern elements of interest, hotspots, or the like) within the design data. For instance, the pre-processed design data 206 may be searchable according to any combination of design data elements including, but not limited to, an identifier of a target pattern, an electrical characteristic of a target pattern, a physical characteristic of a target pattern, or a relationship between a target pattern and one or more additional patterns (e.g. an anchor pattern, a source pattern, or the like), or a graphical representation of a target pattern.

In another embodiment, design data (e.g. raw design data, pre-processed design data 206, or a combination thereof) is stored by the inspection tool 202. For example, the design data may be stored within a memory device 108 of controller 104. In another embodiment, design data may be pre-processed external to the inspection system 100 and stored on the inspection tool 202. In this regard, pre-processed design data 206 associated with one or more samples 110 may be transferred to the inspection tool 202.

In another embodiment, the design module 204 executes a step of analyzing design data 208 stored on the inspection tool 202. In this regard, the design module 204 may identify one or more instances of a target pattern within design data of a sample 110 (e.g. by searching pre-processed design data 206 for instances of one or more target patterns, or the like). Further, the design module 204 may provide parameters of the identified instances of the target patterns necessary for the generation of care areas such as, but not limited to, coordinates and/or the shape of the identified target patterns.

In one embodiment, the inspection tool 202 includes a recipe module 210. For example, the recipe module 210 may generate recipes for one or more inspection steps by the inspection tool 202. In this regard, a recipe may include, but is not limited to, a description of one or more care areas to inspect for defects, one or more registration operations (e.g. to align and/or scale coordinates associated with the design data to coordinates associated with the sample and/or inspection sub-system 102, or the like), one or more defect identification steps, or one or more defect classification steps. Additionally, the generation of design-based care areas on the inspection tool 202 may facilitate efficient multi-step inspection processes (e.g. for systematic defect discovery, or the like). In this regard, design data may be searched on the inspection tool 202 for different target patterns or combinations of target patterns in an iterative inspection analysis without the need for data transfer to external systems.

In another embodiment, the recipe module 210 executes a step 212 of determining one or more target patterns (e.g. one or more pattern elements of interest, one or more hotspots, or the like) associated with fabricated pattern elements on the sample 110 to be inspected by the inspection tool 202 in an inspection step. For example, recipe module 210 may provide one or more target patterns based on one or more objectives of an inspection run of the inspection tool 202. For instance, the recipe module 210 may provide target patterns associated with a known defect type of interest.

In another embodiment, the recipe module 210 determines one or more target patterns in an automated process. For example, the recipe module 210 may analyze the design data 208 of the sample 110 to determine one or more target patterns likely to exhibit defects (e.g. based on characteristics associated with the physical layout, pattern size, proximity to other patterns, circuit complexity, or the like).

In another embodiment, the determination of target patterns is facilitated by a user. For example, a user may provide an input to the inspection tool 202 (e.g. an input to the recipe module 210) including, but not limited to, one or more defect identifiers, one or more GDS coordinates, one or more design-based classification (DBC) clips, or one or more design-based grouping (DBG) bins. In this regard, the recipe module 210 may determine one or more target patterns based on the user input. In another embodiment, the inspection tool 202 may provide a visual display associated with the design data (e.g. within a design view of the inspector tool 202). In this regard, the user may select one or more target patterns from the visual display of the design data. For instance, the visual display may include a graphical display (e.g. a display of an image, or the like) in which design pattern elements (e.g. pattern elements associated with the physical layout of components, pattern elements associated with electrical connections between components, or the like) of the design data may be displayed. As another instance, the visual display may include a text-based display in which design data may be displayed. In another embodiment, a user may visualize (e.g. on a graphical display) design data according to a coordinate system (e.g. GDS coordinates) to determine and/or confirm one or more target patterns. For example, a user may input (e.g. into an input device of the inspection system 100) coordinates to visualize and/or confirm design data at the specified location for the generation of target patterns for inspection.

In another embodiment, the recipe module 210 executes a step 214 of defining one or more care areas to be inspected on the sample 110. For example, the recipe module 210 may define one or more care areas based on the one or more target patterns and the design data stored on the inspection tool 202. In one embodiment, the recipe module 210 interfaces with the design module 204 to analyze the design data based on one or more determined target patterns. In this regard, the recipe module 210 may provide one or more target patterns to the design module 204 for pattern matching. Further, the design module 204 may identify one or more instances of the target patterns within the design data and provide to the recipe module 210 any parameters necessary for the generation of care areas based on the identified instances of the target patterns. For instance, the design module 204 may provide the location (e.g. in design coordinates) of identified instances of the target patterns, the shapes of the identified instances of the target patterns, outlines of the identified instances of the target patterns, or the like.

In another embodiment, the recipe module 210 executes a step 216 of identifying defects on the sample 110. In this regard, the recipe module 210 may interface with the inspection sub-system 102 to perform defect inspection. Further, the recipe module 210 may analyze data received by the inspection sub-system 102 to determine the presence of one or more defects. Additionally, the recipe module 210 may characterize one or more defects. For example, the recipe module may, but is not required to, characterize defects based on a DBC system, a DBG system, or the like. Further, the recipe module 210 may assign one or more defect identifiers to one or more characterized defects.

It is recognized herein that the steps described throughout the present disclosure (e.g. the steps associated with modules of inspection tool 202, or the like) may be carried out by a single controller 104 or, alternatively, multiple controllers 104. It is further noted herein that the one or more controllers 104 may be located proximate to the inspection sub-system 102. Additionally, the one or more controllers 104 may be housed in a common housing with the inspection sub-system 102. Further, any controller 104 or combination of controllers 104 may be separately packaged as a module suitable for integration into a complete inspection system 100. For example, a first controller 104 may be configured to perform the steps associated with the design module 204. One or more additional controllers 104 may then be configured to perform the steps associated with the recipe module 210. In this regard, the one or controllers 104 may be integrated into the inspection system 100.

Figure 3:
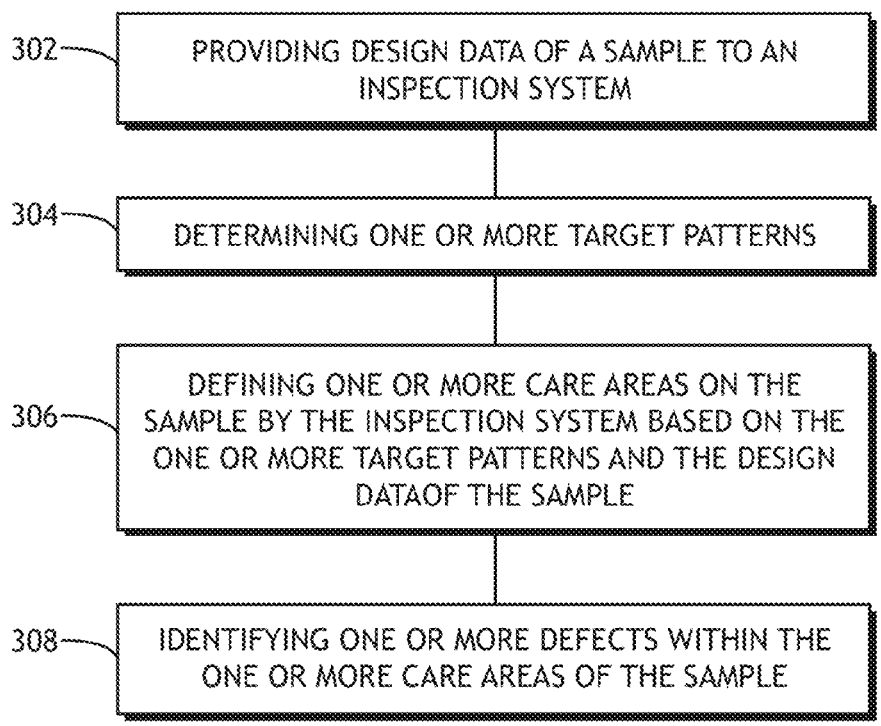
FIG. 3 is a flow diagram illustrating steps performed in a method for defect detection, in accordance with one or more embodiments of the present disclosure.

FIG. 3 is a flow diagram illustrating steps performed in a method 300 for defect detection, in accordance with one or more embodiments of the present disclosure. Applicant notes that the embodiments and enabling technologies described previously herein in the context of system 100 should be interpreted to extend to method 300. It is further noted, however, that the method 300 is not limited to the architecture of system 100.

In one embodiment, the method 300 includes a step 302 of providing design data of a sample to an inspection system. For example, design data may be, but is not required to be, provided to an inspection system in the form of one of more data files (e.g. GDSII files, OASIS files, or the like). In this regard, design data provided to the inspection system may be utilized to generate one or more design-based care areas for inspection.

In another embodiment, the method 300 includes a step 304 of determining one or more target patterns. In this regard, one or more target patterns of interest associated with fabricated features on the sample may be provided for inspection. For example, target patterns may include one or more polygons representative of features to be constructed on a semiconductor layer (e.g. one or more instances of a cross, plus, L-shape, T-shape, square, rectangle, or other polygon with specific dimensions and spacing between instances).

In one embodiment, one or more target patterns are determined based on defect identifiers. In this regard, one or more known defects or defect types associated with defect identifiers (e.g. identifiers used to classify one or more defects, or the like) may be associated with one or more specific target patterns (e.g. based on one or more previous inspection runs, based on one or more design characteristics, or the like). Accordingly, occurrences of the known defects or defect types may be characterized by providing the corresponding target patterns for inspection.

In another embodiment, one or more target patterns are determined based on a previous inspection step (e.g. by the inspection system 100 or an additional inspection system). For example, in systematic defect discovery, a first inspection run on a sample 110 or a portion of the sample 110 may identify one or more fabricated components of the sample 110 prone to defects. In this regard, the first inspection run may determine one or more target patterns associated with the identified fabricated components on the sample 110. Further, a second inspection run may include a recipe (e.g. generated by recipe module 210) to perform a dedicated inspection of the one or more target patterns identified from the first inspection run. In another embodiment, one or more target patterns are determined according to a DBC or a DBG process associated with a previous inspection step.

In another embodiment, one or more target patterns are determined based on one or more coordinates (e.g. GDS coordinates, or the like) of a target pattern on a sample. For example, one or more target patterns may be determined based on known coordinates of an exemplary target pattern of interest associated with the design data. As another example, one or more target patterns may be determined based on known coordinates of an exemplary fabricated component on the sample 110. Accordingly the one or more target patterns associated with the exemplary fabricated component may be provided for inspection.

In another embodiment, the method 300 includes a step 306 of defining one or more care areas on the sample by the inspection system based on the target pattern and the design data of the sample. In this regard, step 306 may include defining one or more areas on the sample to be inspected. For example, a care area may include coordinates on the sample (e.g. in the coordinate system of the inspection system) to be inspected.

In another embodiment, a care area includes one or more target regions on the sample for inspection. For example, a first target region may include one or more instances of a first target pattern identified in step 304, a second target region may include one more instances of a second target pattern identified in step 304, and the like. Further, the definition of one or more target regions may facilitate sensitive inspection of the sample 110. For example, target regions may be defined to include samples with similar sensitivity levels. Accordingly, each target area may be inspected with a different sensitivity threshold such that the contrast of inspection data associated with each target region may be increased.

In another embodiment, step 306 includes identifying one or more instances of target patterns determined in step 304 within the design data (e.g. the pre-processed design data 206 stored in memory device 108 of inspection system 100). In this regard, each identified instance of the target patterns of interest may be included in a care area. Additionally, variations target patterns of interest (e.g. a horizontal and/or vertical flip of a target pattern, a scaled version of a target pattern, a rotated version of a target pattern, or the like) may be identified in step 306 and included in a care area.

Instances of target patterns within device data may be identified using any method known in the art. For example, step 306 may include searching the design data for one or more instances of the target pattern to generate one or more identified instances of the target pattern. In one embodiment, step 306 includes a text-based search of design data. For example, text-based design data (e.g. one or more lists, one or more tables, one or more databases, one or more data files, or the like) may be searched according to one or more characteristics of a target pattern. In another embodiment, step 306 includes an imaged-based search of design data. For example, one or more instances of a target pattern (or a variation of a target pattern) may be found through an image processing algorithm such as, but not limited to, a feature-extraction technique, a convolution technique, pattern-matching technique, a spatial frequency analysis, a transform technique (e.g. a Hough transform technique, or the like). Further, multiple design layers of design data (e.g. corresponding to multiple layers of fabricated components on the sample 110) may be individually searched for one or more instances of target patterns of interest.

In one embodiment, target patterns may be identified using design data contained in a design layout file, such as OASIS or GDS. It is noted herein that the target patterns may vary in size and may be located at various levels of the design data (e.g. associated with various layers, dies, blocks, cells, or the like of the sample 110). In this regard, target patterns in the design data may be identified with a known or observed design cell hierarchy. For example, a design cell hierarchy may be analyzed to identify target patterns in repeating groups within a given set of inspection data.

In another embodiment, the target patterns may be identified utilizing a design rule checking (DRC) process, an optical rule checking (ORC) process, or a failure analysis (FA) process in order to identify target patterns critical to device performance. In another embodiment, the target patterns may be identified utilizing a process window qualification method (PWQ). Searching design data for one or more target patterns may be performed as described in the above-described references by Kulkarni et al. and Zafar et al., which are incorporated above by reference above.

In some embodiments, the target patterns may be identified on the semiconductor wafer utilizing data from electronic design automation (EDA) tools and other knowledge. Any such information about the design generated by an EDA tool may be used to identify the repeating blocks. In addition, the design data may be searched for one or more target patterns in any suitable manner. For example, searching the design data for one or more target patterns may be performed as described in the above-referenced patent applications by Kulkarni et al. and Zafar et al., which are incorporated above by reference. In addition, the target patterns may be selected or identified using any other method or system described in this patent application.

Further, design data may be analyzed in order to identify appropriate target patterns for inspection based on the given inspection technology (e.g., optical inspection, e-beam inspection and the like).

It is recognized that target patterns may be repeated through the die of a sample 110, forming repeating blocks (or fields). In addition, cells of a sample 110 are sometimes repeated through a given die under different names or may be repeated under one name at multiple locations. In some embodiments, repeating cells are aligned on the same horizontal and/or vertical axis. In other embodiments, repeating cells are not aligned on the same horizontal and/or vertical axis.

In another embodiment, step 306 includes providing a confidence metric associated with the identification of each instance of target patterns of interest to locations within design data. In this regard, an instance of a target pattern within device data may include an exact match (e.g. a confidence metric of 100%, or the like) or a substantial match (e.g. a confidence metric less than 100%). It is to be understood that any confidence metric in the art is within the spirit and scope of the present disclosure. For example, a confidence metric may range from 0 (no match) to 1 (exact match).

It is noted herein that care areas may be defined to include a subset of identified instances of target patterns. For example, the probability that a particular defect on a particular component of a device fabricated on a sample 110 will induce a degradation of performance may depend on multiple factors such as, but not limited to, the presence of neighboring structures or operating conditions of the particular component.

In one embodiment, step 306 includes defining one or more care areas to include instances of target patterns proximate to an additional pattern (e.g. a source pattern, an anchor pattern, or the like) within the design data. In this regard, the presence of a source pattern may operate as a filter to provide a subset of instances of target patterns as care areas to be inspected.

Figure 4:
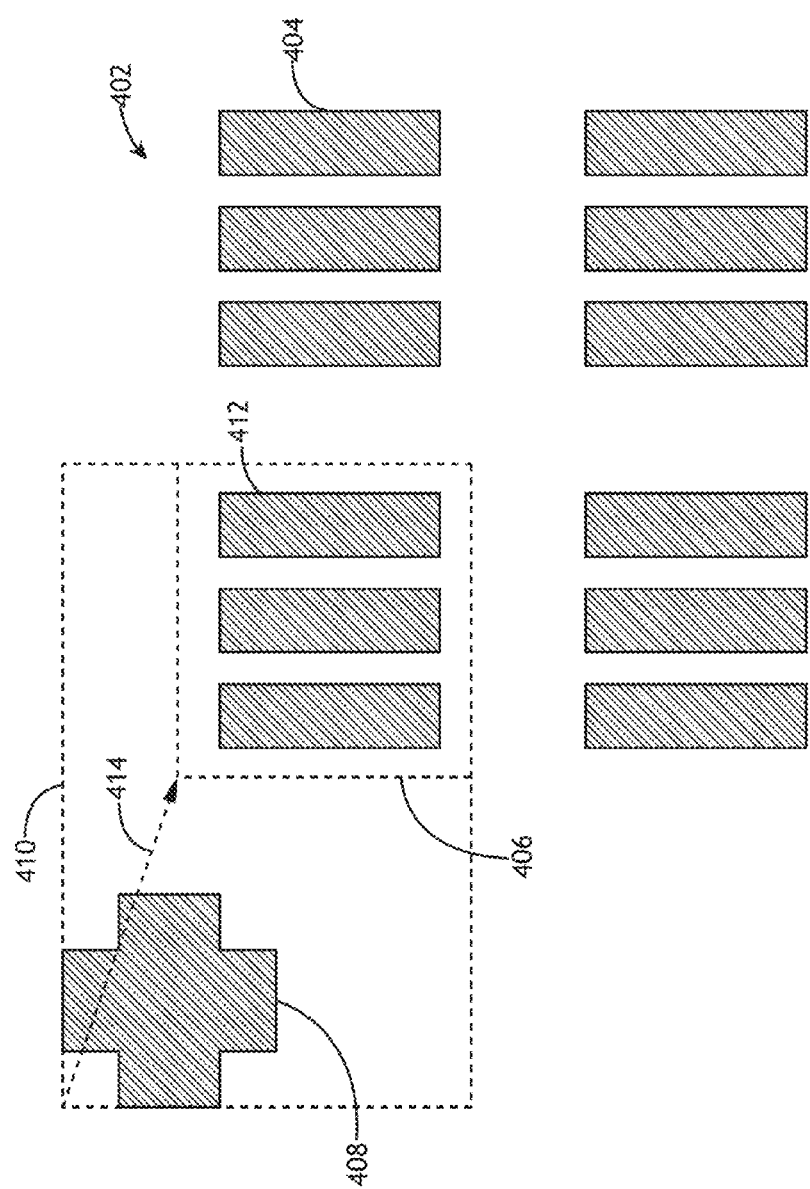
FIG. 4 is a schematic view of design data illustrating the definition of care areas associated based on a source pattern, in accordance with one or more embodiments of the present disclosure.

FIG. 4 is a schematic view of design data illustrating the definition of care areas associated based on a source pattern, in accordance with one or more embodiments of the present disclosure.

In one embodiment, the design data 402 includes multiple instances of target pattern 404. Further, the design data 402 includes a source pattern 408 proximate to the subset of instances of the target pattern 404 (e.g. a particular instance 412 of the target pattern 404). For example, a source pattern 408 may include, but is not limited to one or more instances of a crossing, cross, plus, L-shape, T-shape, square, rectangle, or any other polygon with specific dimensions and spacing between instances.

Further, step 306 may include the definition of a care area 406 around a particular instance 412 of the target pattern 404 based on a spatial relationship between the particular instance 412 of the target pattern 404 and the source pattern 408. For example, a spatial relationship between the particular instance 412 of the target pattern 404 and the source pattern 408 may include, but is not limited to, a vector 414 between the particular instance 412 of the target pattern 404 and the source pattern 408. In another embodiment, step 306 includes searching for one or more instances of the source pattern within the design data and further identifying the subset of instances of the target patterns (e.g. the particular instance 412 of the target pattern 404) for inclusion within a care area based on the spatial relationship between the particular instance 412 of the target pattern 404 and the source pattern 408. In another embodiment, step 306 includes searching for instances of a combined target pattern 410 including the source pattern 408 and an instance of the target pattern within device data 402, while defining a care area 406 around the subset of instances (e.g. the particular instance 412 of the target pattern 404) of the target pattern 404 associated with the identified composite target pattern 410. Accordingly, the source pattern 408 may be utilized as part of a search step, while not being included within the associated care area 406.

In another embodiment, the method 300 includes a step 308 of identifying one or more defects within the one or more care areas of the sample. In this regard, the inspection system (e.g. inspection system 100) inspects the care areas of the sample defined in step 308 for defects (e.g. using illumination sub-system 101). For example, data from inspection sub-system 102 may be analyzed to determine the presence of one or more defects on the sample 110 associated with the care areas defined in step 306. Further, identified defects may be classified (e.g. according to defect identifiers, DBC clips, DBG bins, or the like. In another embodiment, data associated with the one or more identified defects may be provided (e.g. as feed-forward data, feedback data, or the like) to the inspection system 100 and/or external systems.

It is recognized herein that the steps described throughout the present disclosure may be carried out by a single controller 104 or, alternatively, multiple controllers 104. It is further noted herein that the one or more controllers 104 may be housed in a common housing or within multiple housings. In this way, any controller 104 or combination of controllers 104 may be separately packaged as a module suitable for integration into a complete inspection system 100. By way of a non-limiting example, a first controller 104 may be configured to perform the step of identifying a set of illumination detection events based on an illumination signal received from the illumination sensor. One or more additional controllers 104 may then be configured to perform the steps of: identifying a set of radiation detection events based on one or more radiation signals received from the one or more radiation sensors, comparing the set of radiation detection events to the set of illumination detection events to generate a set of coincidence events, and excluding the set of coincidence events from the set of illumination detection events to generate a set of identified features on the sample.

Figure 5A:
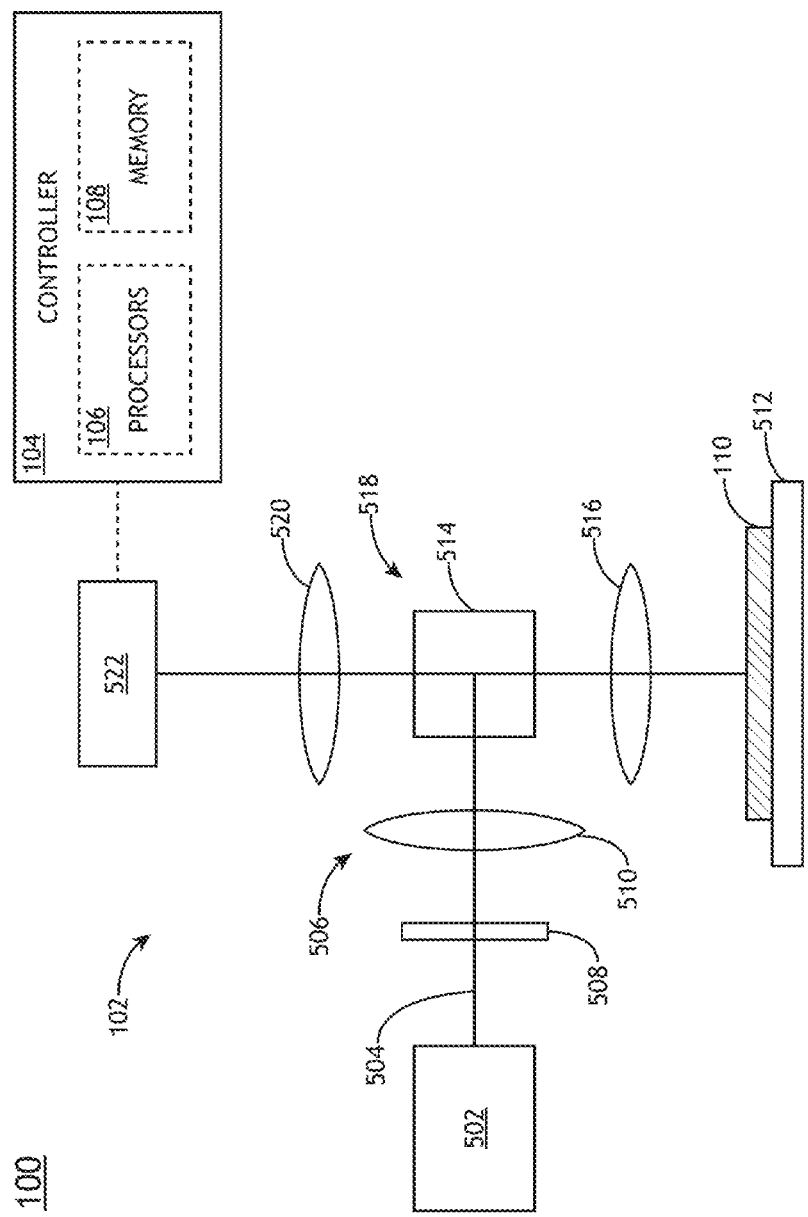
FIG. 5A is a conceptual view illustrating an optical inspection sub-system, in accordance with one or more embodiments of the present disclosure.

FIG. 5A is a conceptual view of an inspection sub-system 102 configured as an optical inspection sub-system, in accordance with one or more embodiments of the present disclosure. In one embodiment, the inspection sub-system 102 includes an illumination source 502. The illumination source 502 may include any illumination source known in the art suitable for generating an illumination beam 504 (e.g. a beam of photons). For example, the illumination source 502 may include, but is not limited to, a monochromatic light source (e.g. a laser), a polychromatic light source with a spectrum including two or more discrete wavelengths, a broadband light source, or a wavelength-sweeping light source. Further, the illumination source 502 may, but is not limited to, be formed from a white light source (e.g. a broadband light source with a spectrum including visible wavelengths), a laser source, a free-form illumination source, a single-pole illumination source, a multi-pole illumination source, an arc lamp, an electrode-less lamp, or a laser sustained plasma (LSP) source. Further, the illumination beam 504 may be delivered via free-space propagation or guided light (e.g. an optical fiber, a light pipe, or the like).

In another embodiment, the illumination source 502 directs the one or more illumination beams 504 to the sample 110 via an illumination pathway 506. The illumination pathway 506 may include one or more lenses 510. Further, the illumination pathway 506 may include one or more additional optical components 508 suitable for modifying and/or conditioning the one or more illumination beams 504. For example, the one or more optical components 508 may include, but are not limited to, one or more polarizers, one or more filters, one or more beam splitters, one or more diffusers, one or more homogenizers, one or more apodizers, or one or more beam shapers. In one embodiment, the illumination pathway 506 includes a beamsplitter 514. In another embodiment, the inspection sub-system 102 includes an objective lens 516 to focus the one or more illumination beams 504 onto the sample 110.

The illumination source 502 may direct the one or more illumination beams 504 to the sample at any angle via the illumination pathway 506. In one embodiment, as shown in FIG. 5A, the illumination source 502 directs the one or more illumination beams 504 to the sample 110 at normal incidence angle. In another embodiment, the illumination source 502 directs the one or more illumination beams 504 to the sample 110 at a non-normal incidence angle (e.g. a glancing angle, a 45-degree angle, or the like).

In another embodiment, the sample 110 is disposed on a sample stage 512 suitable for securing the sample 110 during scanning. In another embodiment, the sample stage 512 is an actuatable stage. For example, the sample stage 512 may include, but is not limited to, one or more translational stages suitable for selectably translating the sample 110 along one or more linear directions (e.g., x-direction ,y-direction and/or z-direction). By way of another example, the sample stage 512 may include, but is not limited to, one or more rotational stages suitable for selectably rotating the sample 110 along a rotational direction. By way of another example, the sample stage 512 may include, but is not limited to, a rotational stage and a translational stage suitable for selectably translating the sample along a linear direction and/or rotating the sample 110 along a rotational direction.

In another embodiment, the illumination pathway 506 includes one or more beam scanning optics (not shown) suitable for scanning the illumination beam 504 across the sample 110. For example, the one or more illumination pathway 506 may include any type of beam scanner known in the art such as, but is not limited to, one or more electro-optic beam deflectors, one or more acousto-optic beam deflectors, one or more galvanometric scanners, one or more resonant scanners, or one or more polygonal scanners. In this way, the surface of a sample 110 may be scanned in an r-theta pattern. It is further noted that the illumination beam 504 may be scanned according to any pattern on the sample. In one embodiment, the illumination beam 504 is split into one or more beams such that one or more beams may be scanned simultaneously.

In another embodiment, the inspection sub-system 102 includes one or more detectors 522 (e.g. one or more optical detectors, one or more photon detectors, or the like) configured to capture radiation emanating from the sample 110 through a collection pathway 518. The collection pathway 518 may include multiple optical elements to direct and/or modify illumination collected by the objective lens 516 including, but not limited to one or more lenses 520, one or more filters, one or more polarizers, one or more beam blocks, or one or more beamsplitters. It is noted herein that components of the collection pathway 518 may be oriented in any position relative to the sample 110. In one embodiment, the collection pathway 518 includes the objective lens 516 oriented normal to the sample 110. In another embodiment, the collection pathway 518 includes multiple collection lenses oriented to collect radiation from the sample at multiple solid angles.

In one embodiment, the inspection system 100 includes a bright-field inspection system. For example, a bright-field image of the sample 110, or a portion of the sample 110, may be projected onto the detector 522 (e.g. by the objective lens 516, the one or more lenses 520, or the like). In another embodiment, the inspection system 100 includes a dark-field inspection system. For example, the inspection system 100 may include one or more components (e.g. an annular beam block, a dark-field objective lens 516 or the like) to direct the illumination beam 504 to the sample 110 at a large incidence angle such that the image of the sample on the detector 110 is associated with scattered and/or diffracted light. In another embodiment, the inspection system 100 includes an oblique angle inspection system. For example, the inspection system 100 may direct the illumination beam 504 to the sample at an off-axis angle to provide contrast for the inspection of defects. In another embodiment, the inspection system 100 includes a phase contrast inspection system. For example, the inspection system 100 may include one or more phase plates and/or beam blocks (e.g. an annular beam block, or the like) to provide a phase contrast between diffracted and undiffracted light from the sample to provide contrast for defect inspection. In another embodiment, the inspection system 100 may include a luminescence inspection system (e.g. a fluorescence inspection system, a phosphorescence inspection system, or the like). For example, the inspection system 100 may direct an illumination beam 504 with a first wavelength spectrum to the sample 110, and include one or more filters to detect one or more additional wavelength spectra emanating from the sample 110 (e.g. emanating from one or more components of the sample 110 and/or one or more defects on the sample 110). In another embodiment, the inspection system includes one or more pinholes located in confocal positions such that the system 100 may operate as a confocal inspection system.

Figure 5B:
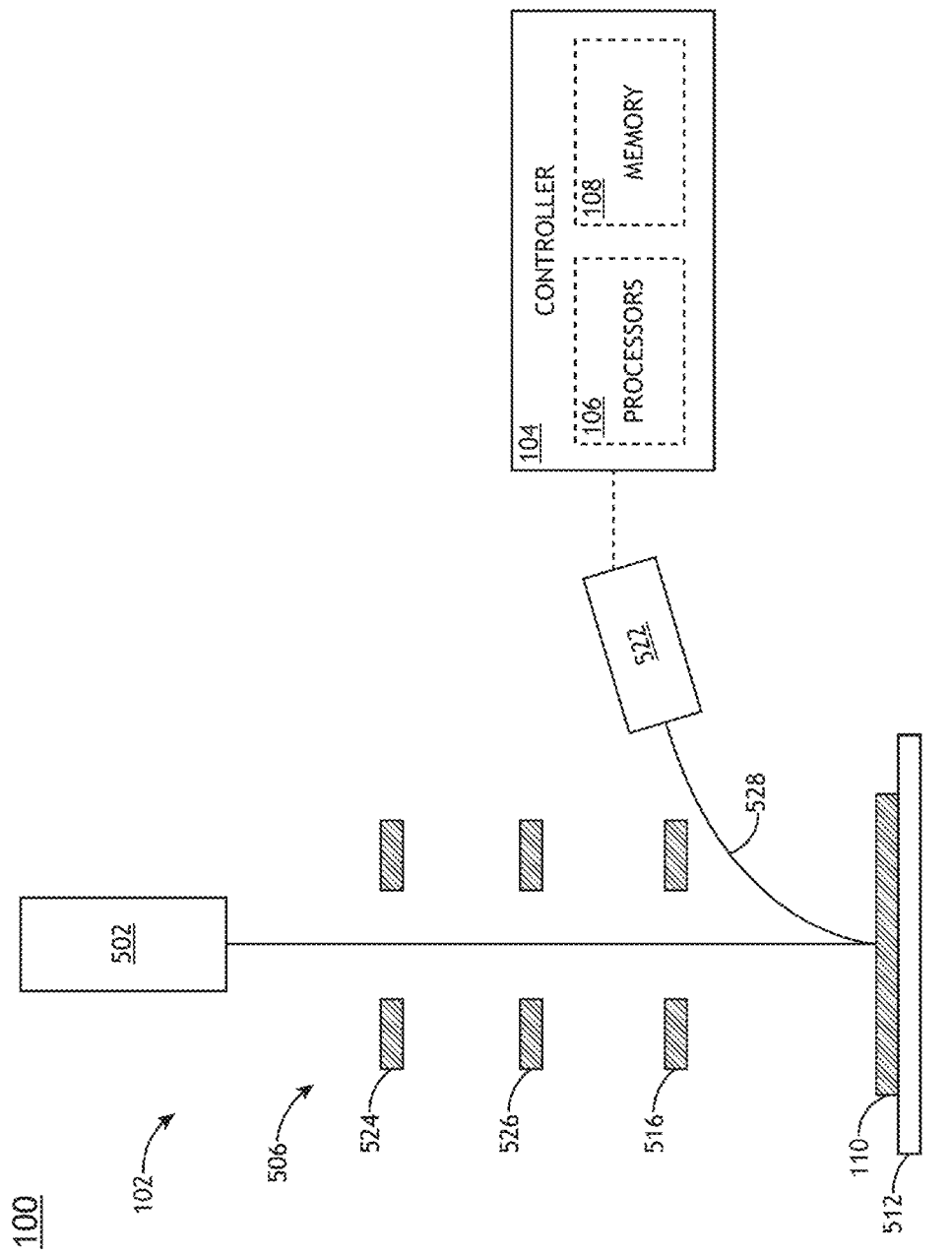
FIG. 5B is a simplified schematic view of an inspection sub-system utilizing one or more particle beams, in accordance with one or more embodiments of the present disclosure.

FIG. 5B is a simplified schematic view of an inspection sub-system configured as a particle beam inspection sub-system in accordance with one or more embodiments of the present disclosure. In one embodiment, the illumination source 502 includes a particle source configured to generate a particle beam 504. The particle source 502 may include any particle source known in the art suitable for generating a particle beam 504. By way of non-limiting example, the particle source 502 may include, but is not limited to, an electron gun or an ion gun. In another embodiment, the particle source 502 is configured to provide a particle beam 504 with a tunable energy. For example, a particle source 502 including an electron source may, but is not limited to, provide an accelerating voltage in the range of 0.1 kV to 30 kV. As another example, a particle source 502 including an ion source may, but is not required to, provide an ion beam with an energy value in the range of 1 to 50 keV.

In another embodiment, the inspection sub-system 102 includes two or more particle beam sources 502 (e.g. electron beam sources or ion beam sources) for the generation of two or more particle beams 504.

In another embodiment, the illumination pathway 506 includes one or more particle focusing elements 524. For example, the one or more particle focusing elements 524 may include, but are not limited to, a single particle focusing element or one or more particle focusing elements forming a compound system. In another embodiment, an objective lens 516 of the system 100 is configured to direct the particle beam 504 to the sample 110. Further, the one or more particle focusing elements 524 and/or the objective lens 516 may include any type of particle lenses known in the art including, but not limited to, electrostatic, magnetic, unipotential, or double-potential lenses. Further, the inspection sub-system 102 may include, but is not limited to one or more electron deflectors, one or more apertures, one or more filters, or one or more stigmators.

In another embodiment, the inspection sub-system 102 includes one or more particle beam scanning elements 526. For example, the one or more particle beam scanning elements may include, but are not limited to, one or more scanning coils or deflectors suitable for controlling a position of the beam relative to the surface of the sample 110. In this regard, the one or more scanning elements may be utilized to scan the particle beam 504 across the sample 110 in a selected pattern.

In another embodiment, the inspection sub-system includes a detector 522 to image or otherwise detect particles 528 emanating from the sample 110. In one embodiment, the detector 522 includes an electron collector (e.g., a secondary electron collector, a backscattered electron detector, or the like). In another embodiment, the detector 522 includes a photon detector (e.g., a photodetector, an x-ray detector, a scintillating element coupled to photomultiplier tube (PMT) detector, or the like) for detecting electrons and/or photons from the sample surface. In a general sense, it is recognized herein that the detector 522 may include any device or combination of devices known in the art for characterizing a sample surface or bulk with a particle beam 504. For example, the detector 522 may include any particle detector known in the art configured to collect backscattered electrons, Auger electrons, transmitted electrons or photons (e.g., x-rays emitted by surface in response to incident electrons, cathodoluminescence of the sample 110, or the like).

In another embodiment, the inspection system 100 includes a voltage contrast imaging (VCI) system. It is recognized herein that inspection systems utilizing particle beams (e.g. electron beams, ion beams, or the like) may be particularly useful for detecting and/or identifying defect mechanisms on a semiconductor sample (e.g. a random logic chip, or the like) due to a high achievable spatial resolution. For example, particle beams may be utilized within an inspection system to image a sample 110 (e.g. by capturing secondary electrons, backscattered electrons, or the like emanating from the sample 110). Additionally, structures on a sample (e.g. a patterned semiconductor wafer) may exhibit charging effects in response to excitation with a particle beam. Charging effects may include a modification of the number of electrons (e.g. secondary electrons) captured by the system and thus the VCI signal strength. In this regard, a voltage contrast imaging (VCI) system may generate a high-resolution image of a sample in which the intensity of each pixel of the image provides data on the electrical properties of the sample at the pixel location. For example, insulating structures and/or structures that are not connected to a ground source (e.g. are not grounded) may develop a charge (e.g. a positive charge or a negative charge) in response to depletion of particles (e.g. secondary electrons, ions, or the like) induced by the particle beam. Accordingly the induced charge may deflect the trajectories of secondary electrons and reduce the signal intensity captured by a detector. Conversely, grounded structures may not develop a charge and therefore may exhibit a strong signal (e.g. appear bright in an associated VCI image). Further, the signal strength of capacitive structures may be a function of the scan speed and/or the energy of the particle beam. In this regard, a VCI image may include a grayscale image in which the grayscale value of each pixel provides data on the relative electrical characteristics of that location on the wafer. In a further embodiment, the inspection system 100 includes one or more components (e.g. one or more electrodes) configured to apply one or more voltages to one or more locations of the sample 110. In this regard, the system 100 may generate active voltage contrast imaging data.

In another embodiment, the inspection system 100 may include a display (not shown). In another embodiment, the display is communicatively coupled to the controller 104. For example, the display may be communicatively coupled to one or more processors 106 of controller 104. In this regard, the one or more processors 106 may display one or more of the various results of the present invention on display.

The display device may include any display device known in the art. In one embodiment, the display device may include, but is not limited to, a liquid crystal display (LCD). In another embodiment, the display device may include, but is not limited to, an organic light-emitting diode (OLED) based display. In another embodiment, the display device may include, but is not limited to a CRT display. Those skilled in the art should recognize that a variety of display devices may be suitable for implementation in the present invention and the particular choice of display device may depend on a variety of factors, including, but not limited to, form factor, cost, and the like. In a general sense, any display device capable of integration with a user interface device (e.g., touchscreen, bezel mounted interface, keyboard, mouse, trackpad, and the like) is suitable for implementation in the present invention.

In another embodiment, the inspection system 100 may include a user interface device (not shown). In one embodiment, the user interface device is communicatively couple to the one or more processors 106 of controller 104. In another embodiment, the user interface device may be utilized by controller 104 to accept selections and/or instructions from a user. In some embodiments, described further herein, the display may be used to display data to a user. In turn, a user may input selection and/or instructions (e.g., a user selection of inspection regions) responsive to inspection data displayed to the user via display device.

The user interface device may include any user interface known in the art. For example, the user interface may include, but is not limited to, a keyboard, a keypad, a touchscreen, a lever, a knob, a scroll wheel, a track ball, a switch, a dial, a sliding bar, a scroll bar, a slide, a handle, a touch pad, a paddle, a steering wheel, a joystick, a bezel input device or the like. In the case of a touchscreen interface device, those skilled in the art should recognize that a large number of touchscreen interface devices may be suitable for implementation in the present invention. For instance, the display device may be integrated with a touchscreen interface, such as, but not limited to, a capacitive touchscreen, a resistive touchscreen, a surface acoustic based touchscreen, an infrared based touchscreen, or the like. In a general sense, any touchscreen interface capable of integration with the display portion of the display device is suitable for implementation in the present invention. In another embodiment, the user interface may include, but is not limited to, a bezel mounted interface.

It is noted herein that FIGS. 5A and 5B, along with the corresponding descriptions above, are provided merely for illustration and should not be interpreted as limiting. It is anticipated that a number of equivalent or additional configurations may be utilized within the scope of the present invention.

The herein described subject matter sometimes illustrates different components contained within, or connected with, other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "connected", or "coupled", to each other to achieve the desired functionality, and any two components capable of being so associated can also be viewed as being "couplable", to each other to achieve the desired functionality. Specific examples of couplable include but are not limited to physically interactable and/or physically interacting components and/or wirelessly interactable and/or wirelessly interacting components and/or logically interactable and/or logically interacting components.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes. Furthermore, it is to be understood that the invention is defined by the appended claims.

What is claimed:

1. A defect inspection system, comprising:
   an inspection sub-system, comprising:
      an illumination source configured to generate a beam of illumination;
      a set of illumination optics to direct the beam of illumination to a sample; and
      a detector configured to collect illumination emanating from the sample; and
   a controller communicatively coupled to the detector, the controller including a memory device and one or more processors configured to execute program instructions configured to cause the one or more processors to:
      store design data of a sample within the memory device of the controller, wherein the design data is pre-processed to include a searchable dataset suitable for identifying patterns of interest within the design data, wherein the design data is registered to the inspection sub-system to provide locations of identified patterns of interest in coordinates of the inspection sub-system;
      determine one or more target patterns as patterns of interest corresponding to one or more features on the sample;
      define one or more care areas on the sample based on identifying instances of the one or more target patterns within the design data stored within the memory device of the controller; and
      identify one or more defects within the one or more care areas of the sample based on the illumination collected by the detector during inspection of the one or more care areas with the illumination sub-system.

2. The defect inspection system of claim 1, wherein identifying the one or more instances of the one or more target patterns within the design data of the sample comprises:
   generating a composite search pattern, wherein the composite search pattern includes a source pattern and at least one target pattern of the one or more target patterns;
   identifying one or more instances of the composite pattern within the design data of the sample; and
   identifying the one or more instances of the one or more target patterns within the design data of the sample based on the one or more identified instances of the composite pattern.

3. The defect inspection system of claim 1, wherein identifying the instances of the one or more target patterns within the design data of the sample comprises:
   searching the design data for the one or more target patterns to generate one or more identified instances of the one or more target patterns.

4. The defect inspection system of claim 1, wherein defining the one or more care areas comprises:
   identifying instances of the one or more target patterns within the design data;
   determining a confidence score for each instance of the one or more target patterns within the design data, the confidence score a measure of a similarity between the one or more target patterns and the identified instances of the one or more target patterns within the design data; and
   defining, as the one or more care areas instances of the one or more target patterns within the design data having a confidence score above a selected confidence score.

5. The defect inspection system of claim 1, wherein defining the one or more care areas on the sample comprises:

defining one or more target regions, wherein the one or more target regions include at least one instance of at least one of the one or more target patterns, wherein the care areas include the one or more target regions; and
defining an inspection sensitivity for each of the one or more target regions.

6. The defect inspection system of claim 5, wherein
the inspection sensitivity of each of the one or more target regions is individually adjustable.

7. The defect inspection system of claim 1, wherein the one or more target patterns comprise:
one or more target patterns identified by at least one of a design-based classification or a design-based binning process.

8. The defect inspection system of claim 1, wherein the one or more target patterns comprise:
one or more target patterns associated with one or more known defect types.

9. The defect inspection system of claim 1, wherein the one or more target patterns comprise:
one or more target patterns identified by a previous defect inspection process.

10. The defect inspection system of claim 1, wherein determining the one or more target pattern comprises:
determining the one or more target patterns by a user.

11. The defect inspection system of claim 10, wherein determining the one or more target patterns by the user comprises:
selecting one or more instances of the one or more target patterns from the design data of the sample.

12. The defect inspection system of claim 11, wherein selecting the one or more instances of the one or more target patterns from the design data of the sample comprises:
selecting the one or more instances of the one or more target patterns from a visual display of the design data of the sample.

13. The defect inspection system of claim 1, wherein defining the one or more care areas comprises:
determining one or more coordinates associated with one or more instances of the one or more target patterns within the design data of the sample.

14. The defect inspection system of claim 1, wherein the one or more processors are further configured to execute program instructions causing the one or more processors to:
determine one or more additional target patterns as patterns of interest based on the one or more identified defects;
define one or more additional care areas on the sample based on identifying instances of the one or more additional target patterns within the design data stored within the memory device of the controller; and
identify one or more additional defects within the one or more additional care areas based on inspection with a virtual inspection system.

15. The defect inspection system of claim 1, wherein the design data comprises:
at least one of a physical layout of the sample or an electrical layout of the sample.

16. The defect inspection system of claim 1, further comprising:
providing the one or more care areas for use in a subsequent inspection process.

17. The defect inspection system of claim 1, further comprising:
classifying one or more identified defects based on the design data of the sample.

18. The defect inspection system of claim 1, wherein the beam of illumination comprises:
at least one of a beam of photons or a beam of particles.

19. The defect inspection system of claim 18, wherein the beam of particles comprises:
at least one of a beam of electrons or ions.

20. The defect inspection system of claim 1, wherein the set of illumination optics comprises:
at least one of photon optics or particle optics.

21. The defect inspection system of claim 1, wherein the detector comprises:
at least one of a photon detector, or a particle detector.

22. The defect inspection system of claim 1, wherein the controller is located proximate to the inspection sub-system.

23. The defect inspection system of claim 1, wherein the controller and at least a portion of the inspection sub-system are located within a common housing.

24. The defect inspection method of claim 1, wherein determining the one or more target patterns comprises:
providing one or more coordinates associated with one or more instances of the one or more target patterns within the design data of the sample.

25. The defect inspection system of claim 1, wherein the one or more processors are further configured to execute program instructions causing the one or more processors to:
determine one or more additional target patterns as patterns of interest based on the one or more identified defects;
define one or more additional care areas on the sample based on identifying instances of the one or more additional target patterns within the design data stored within the memory device of the controller; and
identify one or more additional defects within the one or more additional care areas based on illumination collected by the detector during inspection of the one or more additional care areas with the illumination sub-system.

26. The defect inspection system of claim 1, wherein the inspection system is a virtual inspection system.

27. A defect inspection system, comprising:
an inspection sub-system, comprising:
an illumination source configured to generate a beam of illumination;
a set of illumination optics to direct the beam of illumination to a sample;
a detector configured to collect illumination emanating from the sample; and
a controller communicatively coupled to the detector, the controller including a memory device and one or more processors configured to execute program instructions configured to cause the one or more processors to:
determine one or more target patterns corresponding to one or more features on the sample;
determine a source pattern, wherein the source pattern is proximate to a subset of instances of the one or more target patterns within design data of the sample, wherein the design data of the sample is stored within the memory device of the controller;
define a spatial relationship between the source pattern and the at least one target pattern of the subset of instances of the one or more target patterns within the design data of the sample;
identify one or more instances of the source pattern within the design data of the sample;
identify the subset of instances of the one or more target patterns within the design data of the sample based on the one or more identified instances of the source pattern and the spatial relationship between the source pattern and the at least one target pattern of the subset of instances of the one or more target patterns;

define one or more care areas on the sample based on the subset of instances of the one or more target patterns; and identify one or more defects within the one or more care areas of the sample based on the illumination collected by the detector.

28. A defect inspection method, comprising:

storing design data of a sample in a memory device of an inspection system, wherein the design data is pre-processed to include a searchable dataset suitable for identifying patterns of interest within the design data, wherein the design data is registered to provide coordinates of identified patterns of interest in coordinates of the inspection sub-system;

determining, with one or more processors of the inspection system, one or more target patterns as patterns of interest corresponding to one or more features on the sample;

defining, with one or more processors of the inspection system, one or more care areas on the sample by the inspection system based on identifying instances of the one or more target patterns within the design data of the sample;

inspecting the one or more care areas of the sample with the inspection system by illuminating the one or more care areas with a beam of illumination and collecting illumination emanating from the sample with a detector; and identifying, with one or processors of the inspection system, one or more defects within the one or more care areas of the sample based on the illumination collected by the detector.

29. The defect inspection method of claim 28, wherein defining the one or more care areas comprises:

determining a source pattern, wherein the source pattern is proximate to a subset of instances of the one or more target patterns within the design data of the sample;

defining a spatial relationship between the source pattern and at least one target pattern of the subset of instances of the one or more target patterns within the design data of the sample;

identifying one or more instances of the source pattern within the design data of the sample; and identifying the subset of instances of the one or more target patterns within the design data of the sample based on the one or more identified instances of the source pattern and the spatial relationship between the source pattern and the at least one target pattern of the subset of instances of the one or more target patterns.

30. The defect inspection method of claim 28, wherein identifying the instances of the one or more target patterns within the design data of the sample comprises:

searching the design data for the one or more target patterns to generate the identified instances of the one or more target patterns.

31. The defect inspection method of claim 30, wherein defining the one or more care areas comprises:

identifying instances of the one or more target patterns within the design data;

determining a confidence score for each instance of the one or more target patterns within the design data, the confidence score a measure of a similarity between the one or more target patterns and the one or more identified instances of the one or more target patterns within the design data; and defining, as the one or more care areas instances of the one or more target patterns within the design data having a confidence score above a selected confidence score.

32. The defect inspection method of claim 28, wherein the one or more target patterns comprise:

one or more target patterns identified by at least one of a design-based classification or a design-based binning process.

33. The defect inspection method of claim 28, wherein the one or more target patterns comprise:

one or more target patterns identified by a previous defect inspection process.

34. The defect inspection method of claim 28, wherein determining the one or more target patterns comprises:

determining the one or more target patterns by a user.

35. The defect inspection method of claim 34, wherein determining the one or more target patterns by a user comprises:

selecting one or more instances of the one or more target patterns from the design data of the sample.

36. The defect inspection method of claim 35, wherein selecting the one or more instances of the one or more target patterns from the design data of the sample comprises:

selecting one or more instances of the one or more target patterns from a visual display of the design data of the sample.

37. The defect inspection method of claim 33, further comprising:

determining one or more additional target patterns as patterns of interest based on the one or more identified defects;

defining one or more additional care areas on the sample based on identifying instances of the one or more additional target patterns within the design data stored within the memory device of the controller; and identifying one or more additional defects within the one or more additional care areas based on inspection with a virtual inspection system.

38. The defect inspection method of claim 33, wherein the design data comprises:

at least one of a physical layout of the sample or an electrical layout of the sample.

39. The defect inspection method of claim 33, further comprising:

providing the one or more care areas for use in a subsequent inspection process.

40. The defect inspection method of claim 28, further comprising:

classifying one or more identified defects based on the design data of the sample.

41. A defect inspection system, comprising:

an inspection sub-system, comprising:

an illumination source configured to generate a beam of illumination;

a set of illumination optics to direct the beam of illumination to a sample;

a detector configured to collect illumination emanating from the sample; and a controller communicatively coupled to the detector, the controller including a memory device and one or more processors configured to execute program instructions configured to cause the one or more processors to:

determine one or more target patterns as patterns of interest corresponding to one or more features on the sample;

generate a composite search pattern, wherein the composite search pattern includes a source pattern and at least one target pattern of the one or more target patterns;

define one or more care areas on the sample based on identifying one or more instances of the composite pattern within the design data of the sample, wherein the design data of the sample is stored within the memory device of the controller; and identify one or more defects within the one or more care areas of the sample based on illumination collected by the detector during inspection of the one or more care areas with the illumination sub-system.

42. The defect inspection system of claim 41, wherein identifying the instances of the one or more target patterns within the design data of the sample comprises:

searching the design data for the one or more target patterns to generate one or more identified instances of the one or more target patterns.

43. The defect inspection system of claim 41, wherein defining the one or more care areas comprises:

identifying instances of the one or more target patterns within the design data;

determining a confidence score for each instance of the one or more target patterns within the design data, the confidence score a measure of a similarity between the one or more target patterns and the identified instances of the one or more target patterns within the design data; and defining, as the one or more care areas, instances of the one or more target patterns within the design data having a confidence score above a selected confidence score.

44. The defect inspection system of claim 41, wherein the one or more target patterns comprise:

one or more target patterns identified by a previous defect inspection process.

45. The defect inspection system of claim 41, wherein determining the one or more target pattern comprises:

determining the one or more target patterns by a user.

46. The defect inspection system of claim 45, wherein determining the one or more target patterns by the user comprises:

selecting one or more instances of the one or more target patterns from the design data of the sample.

47. The defect inspection system of claim 46, wherein selecting the one or more instances of the one or more target patterns from the design data of the sample comprises:

selecting the one or more instances of the one or more target patterns from a visual display of the design data of the sample.

\* \* \* \* \*